United States Patent
Stefan et al.

(10) Patent No.: US 9,429,204 B2
(45) Date of Patent: Aug. 30, 2016

(54) HOLDING DEVICE FOR MEDICAL INSTRUMENTS

(75) Inventors: Jochen Stefan, Wald (DE); Uwe Bacher, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 385 days.

(21) Appl. No.: 12/966,762

(22) Filed: Dec. 13, 2010

(65) Prior Publication Data

US 2011/0147556 A1    Jun. 23, 2011

(30) Foreign Application Priority Data

Dec. 23, 2009    (DE) .................. 10 2009 060 495

(51) Int. Cl.
| | |
|---|---|
| *A47F 5/00* | (2006.01) |
| *A61B 1/00* | (2006.01) |
| *F16F 1/02* | (2006.01) |
| *E04G 3/00* | (2006.01) |
| *A61B 18/18* | (2006.01) |
| *F16M 11/10* | (2006.01) |
| *F16M 13/02* | (2006.01) |
| *A61M 25/01* | (2006.01) |
| *A61B 17/00* | (2006.01) |

(52) U.S. Cl.
CPC ........... *F16F 1/021* (2013.01); *A61B 1/00149* (2013.01); *A61B 2017/00867* (2013.01); *A61B 2090/5025* (2016.02); *A61M 25/0141* (2013.01); *A61M 2205/0266* (2013.01); *F16F 2224/0258* (2013.01); *F16F 2230/0011* (2013.01); *F16M 11/10* (2013.01); *F16M 13/02* (2013.01); *F16M 13/022* (2013.01)

(58) Field of Classification Search
CPC .............. A61B 1/0051; A61B 1/0058; A61B 1/00149; A61M 25/0147; A61M 2205/0266; A61M 25/0141; F16M 13/02; F16M 11/10; F16M 11/04; F16M 13/022; F16F 1/021
USPC ................ 248/288.11, 288.51, 274.1, 276.1, 248/282.1, 284.1; 600/141–143; 606/19
See application file for complete search history.

(56) References Cited

U.S. PATENT DOCUMENTS

| | | | | |
|---|---|---|---|---|
| 1,272,845 A | * | 7/1918 | Peck et al. .................... | 248/586 |
| 3,679,174 A | * | 7/1972 | Boettcher ...................... | 254/45 |

(Continued)

FOREIGN PATENT DOCUMENTS

| | | |
|---|---|---|
| DE | 10314156 B3 | 1/2005 |
| DE | 10334135 A1 | 3/2005 |

(Continued)

OTHER PUBLICATIONS

European Search Report; Application No. EP 10 01 5162; Issued: May 10, 2011; 4 pages.

*Primary Examiner* — Syed A Islam
*Assistant Examiner* — Taylor Morris
(74) *Attorney, Agent, or Firm* — Whitmyer IP Group LLC

(57) ABSTRACT

A holding device for medical instruments, having a bracket on which at least one medical instrument can be affixed, at least one joint to position the bracket and a weight-relieving system to compensate the bracket load. The holding device is of compact and light structure and for cleaning purposes is completely autoclavable together with the bracket. The weight-relieving system is configured as a resetting element that is coupled with the bracket and is made of a material that essentially includes a plateau stress.

18 Claims, 3 Drawing Sheets

(56) References Cited

U.S. PATENT DOCUMENTS

| | | | | |
|---|---|---|---|---|
| 4,151,754 | A * | 5/1979 | Reist | 74/89.2 |
| 4,541,584 | A * | 9/1985 | Rivinius | 242/486.6 |
| 5,275,379 | A * | 1/1994 | McAleer | 254/372 |
| 5,348,259 | A * | 9/1994 | Blanco et al. | 248/276.1 |
| 5,402,690 | A * | 4/1995 | Sekiguchi et al. | 74/490.01 |
| 5,436,542 | A | 7/1995 | Petelin et al. | |
| 5,465,946 | A * | 11/1995 | Smith | 269/75 |
| 6,371,463 | B1 * | 4/2002 | Sorovshian | 267/158 |
| 6,491,273 | B2 * | 12/2002 | King et al. | 248/276.1 |
| 6,835,083 | B1 * | 12/2004 | Alacqua et al. | 439/310 |
| 6,896,230 | B2 * | 5/2005 | Cvek | 248/276.1 |
| 7,255,311 | B2 * | 8/2007 | Metelski | 248/123.11 |
| 7,637,466 | B2 * | 12/2009 | Dillard | 248/280.11 |
| 8,132,769 | B2 * | 3/2012 | Metelski | 248/281.11 |
| 8,205,845 | B2 * | 6/2012 | Hammer | 248/276.1 |
| 2004/0054322 | A1 | 3/2004 | Vargas | |
| 2007/0129634 | A1 * | 6/2007 | Hickey et al. | 600/439 |
| 2007/0276437 | A1 * | 11/2007 | Call et al. | 606/232 |
| 2008/0237413 | A1 * | 10/2008 | Hammer | 248/125.1 |

FOREIGN PATENT DOCUMENTS

| | | |
|---|---|---|
| DE | 102005054010 A1 | 5/2007 |
| DE | 102008011639 A1 | 9/2009 |
| EP | 1586925 A1 | 10/2005 |
| WO | 03099152 A1 | 12/2003 |
| WO | WO 2007039271 A2 * | 4/2007 |
| WO | 2007054327 A1 | 5/2007 |

\* cited by examiner

HOLDING DEVICE FOR MEDICAL INSTRUMENTS

CROSS-REFERENCE TO RELATED APPLICATIONS

The present application claims priority of German patent application No. 10 2009 060 495.2 filed on Dec. 23, 2009, the content of which is incorporated herein by reference.

FIELD OF THE INVENTION

The invention relates to a holding device for medical instruments, with a bracket on which at least one medical instrument can be affixed, with at least one joint to position the bracket and with a weight-relieving system to compensate the bracket load.

BACKGROUND OF THE INVENTION

Holding devices of this type are often required in executing surgical procedures, to hold medical instrument of the most varied types, such as retractors, video cameras or endoscopes, in a certain position for extended periods. As a result of the jointed configuration of the holding device, it is possible for the surgeon to precisely position the medical instrument held by the bracket and to stabilize the selected position of the holding device by blocking the joint or joints of the bracket.

To facilitate for the operator the handling of such a holding device together with a medical instrument, these holding devices are often provided with a weight-relieving system to compensate the bracket load of the holding device. The weight-relieving system, usually in the form of counterweights or spring packets, is intended to balance out the actual weight of the bracket along with medical instruments attached thereto, so that the operator can pivot the holding device in every desired position virtually free of weight.

A generic holding device with a weight-relieving system is known for example from DE 10 2005 054 010 A1. With this known holding device, the weight-relieving system consists of a linear spring arrangement with several spring blocks that are positioned parallel to one another and engage on the pivot joint of the bracket via a cam support.

With this known spring arrangement, it is possible to displace the holding device essentially free of weight, but this spring arrangement, like the constructions with counterweights as weight-relieving systems as known in the art, has the disadvantage that these systems take up considerable volume and in addition have great weight, and thus these known holding devices can rarely be disassembled after each use and autoclaved for cleaning purposes.

SUMMARY OF THE INVENTION

Consequently it is the object of the invention to provide a holding device for medical instruments of the aforementioned type, whose weight-relieving system is of compact, light structure and for cleaning purposes can be completely autoclaved together with the bracket.

This object is achieved by the invention in that the weight-relieving system is configured as a resetting element coupled with the bracket, made of a material that essentially has a plateau stress.

Materials that have a plateau stress are distinguished in that these materials have an essentially horizontal-running stress plateau in the stress-strain diagram, which depicts the length modification (expansion) of a material depending on a tractive force (tractive stress) that attacks the material. This means that a length modification (expansion) of the material can be produced in this particular area, which constitutes the plateau, without a higher or at least only slightly higher force (tractive stress) having to be exerted than before and behind the stress plateau.

Because of the inventive configuration of the weight-relieving system as a resetting element acting on the bracket, it is possible to make the weight-relieving system as a compact, light construction so that the entire holding device can easily be disassembled and autoclaved for cleaning purposes.

According to a practical embodiment of the invention it is proposed that the material of the resetting element that has a plateau stress should be a CuZnAl, FeNiCoTi or NiTi alloy.

It is proposed with a preferred embodiment of the invention that the material that has a plateau stress should be a shape-memory alloy.

Shape-memory alloys are distinguished in that they can resume their original shape after a relatively strong deformation. In conjunction with a shape-memory alloy this means that the material that has been extended in the area of its stress plateau without additional force being exerted resumes its original shape after the tractive stress has been discontinued.

According to a practical embodiment of the invention, it is proposed that the shape-memory alloy that constitutes the resetting element should be an NiTi alloy, in particular NiTiNoI. The intermetallic alloy NiTiNoI is distinguished by a stress plateau in the area of an expansion of 1% to 8%. This means that an NiTiNoI element that is pre-stressed to 1% expansion can be expanded up to 8% without additional force being exerted, such that the NiTiNoI element in addition resumes its original length after removal of the tractive stress because of its shape-memory property.

To make possible a largely force-free actuation of the bracket, it is proposed according to the invention that the resetting element should be pre-stressed by the bracket load until reaching the plateau stress, so that the additional expansion of the resetting element falls directly into the force-free area of the stress plateau.

According to a practical embodiment of the invention it is proposed that the resetting element, straddling the at least one joint, should be coupled with the bracket so that the resetting element is tensed or decontracted again by the actuation of the joint.

With a first practical embodiment to configure the resetting element it is proposed that the resetting element should be configured as a cable winch.

According to an alternative second embodiment it is proposed that the resetting element should be configured as a spring element.

The cable winch that constitutes the weight-relieving system is advantageously coupled with the bracket in such a way that the cable winch is mounted with one end on a first bracket part and with the other end mounted on a second bracket part that can be displaced by the at least one joint with respect to the first bracket part.

It is further proposed with the invention that the cable winch should be mounted on the displaceable bracket part by means of a flexible element, for example a link chain. The coupling of the cable winch with the displaceable bracket part by the link chain makes possible a uniform, non-jerking transmission of the forces exerted by the displaceable bracket part onto the cable winch that constitutes the weight-relieving system.

It is finally proposed with the invention that the cable winch should be mounted in a guide tube in order to ensure a secure, undisturbed storage and guidance of the link chain.

According to a preferred embodiment of the invention it is proposed that the guide tube should be mounted so that it can slide axially on the bracket, so that the pre-tensing of the cable winch on the plateau stress can be adjusted advantageously by the axially moveable guide tube in which the cable winch is mounted.

Further properties and advantages of the invention can be seen from the attached drawings, in which an embodiment of an inventive holding device for medical instruments is depicted by way of example without restricting the invention to this embodiment.

DETAILED DESCRIPTION OF THE INVENTION

Figure 1:
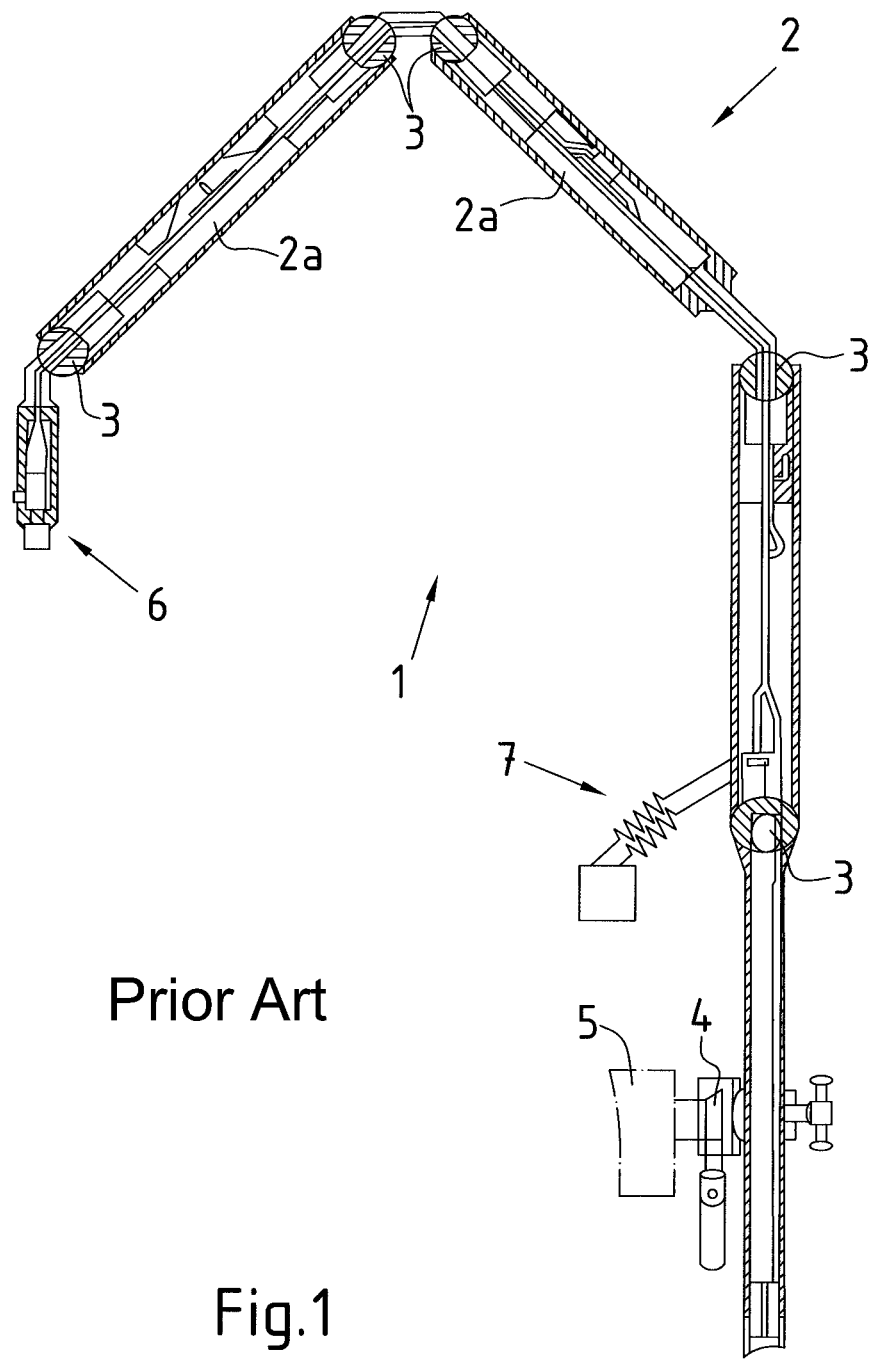
FIG. 1 shows a holding device for medical instruments according to the state of the art.

FIG. 1 shows a holding device 1 for medical instruments according to the state of the art.

This holding device 1 consists essentially of a bracket 2 made up of several bracket parts 2a, such that the individual bracket parts 2a of the bracket are connected with one another so that they can rotate with respect to one another by a joint 3 configured as a ball and socket joint 3.

Holding devices 1 of this type are frequently required in executing surgical procedures in order to hold medical instruments of many types, such as retractors, microscopes, video cameras or endoscopes, in a certain position for an extended period. As a result of the jointed configuration of the holding device 1 it is possible for the surgeon to precisely position the medical instrument and to fix the selected position of the holding device 1 by blocking the joint 3 or joints 3. In addition to endoscopic surgery, such holding devices 1 find application in open or invasive surgery.

The bracket 2 can be affixed in the area of its proximal end, for example on the operating table 5, by a jig 4. On the distal end the bracket 2 comprises an instrument insertion 6 for inserting the medical instrument that is to be positioned by the holding device 1.

Alternatively to the structure of the bracket 2, as shown in FIG. 1, with several successive coupled bracket parts 2a that are connected with one another by joints 3, it is also possible of course to configured the bracket 2 with several arms in such a way that several bracket parts 2a extend from a joint 3 in various directions. Said bracket parts 2a in turn can be coupled with additional bracket parts 2a by joints 3 and can be outfitted on their distal ends in each case with instrument insertions 6 to insert the medical instruments that are to be positioned by the holding device 1.

In addition, alternatively to the mounting of the bracket 2 on an operating table 5 as shown in FIG. 1, it is possible to mount the bracket 2 so that it can pivot on the ceiling, on a wall or on the floor.

To facilitate for the operator the handling of such a holding device 1 complete with a medical instrument, the holding device 1 is provided with a weight-relieving system 7 to compensate the bracket load of the holding device 1. The illustrated weight-relieving system 7 in the form of spring packets serves to balance out the actual weight of the bracket 2 along with the medical instruments attached thereto, so that the operator can pivot the holding device 1 into every desired position virtually free of weight.

Figure 2:
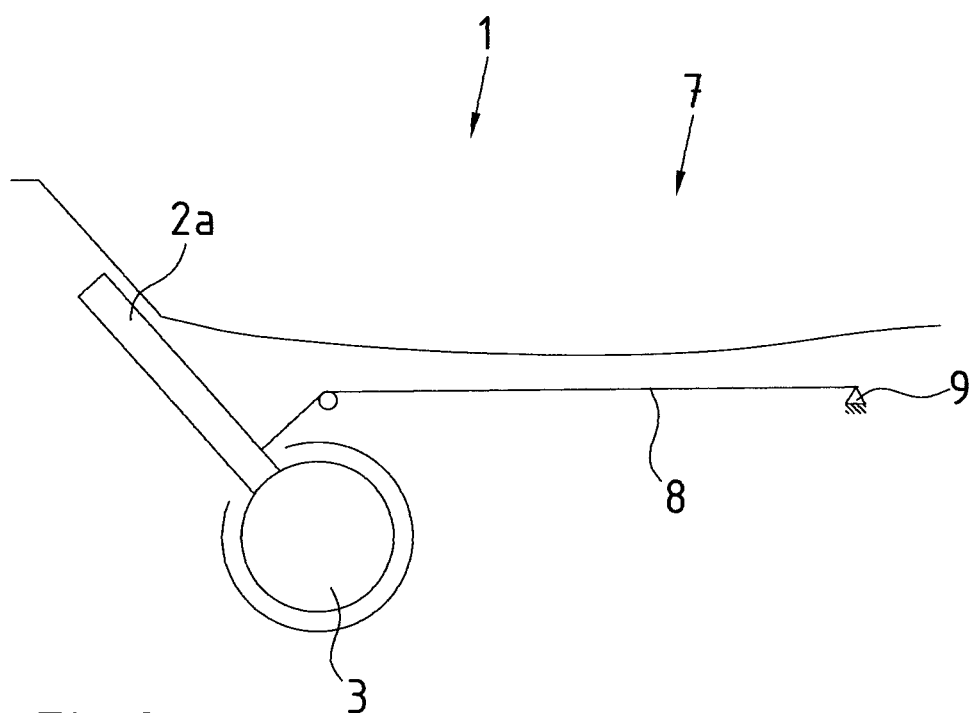
FIG. 2 shows a schematic sketch of the structure of an inventive holding device for medical instruments.
Figure 3:
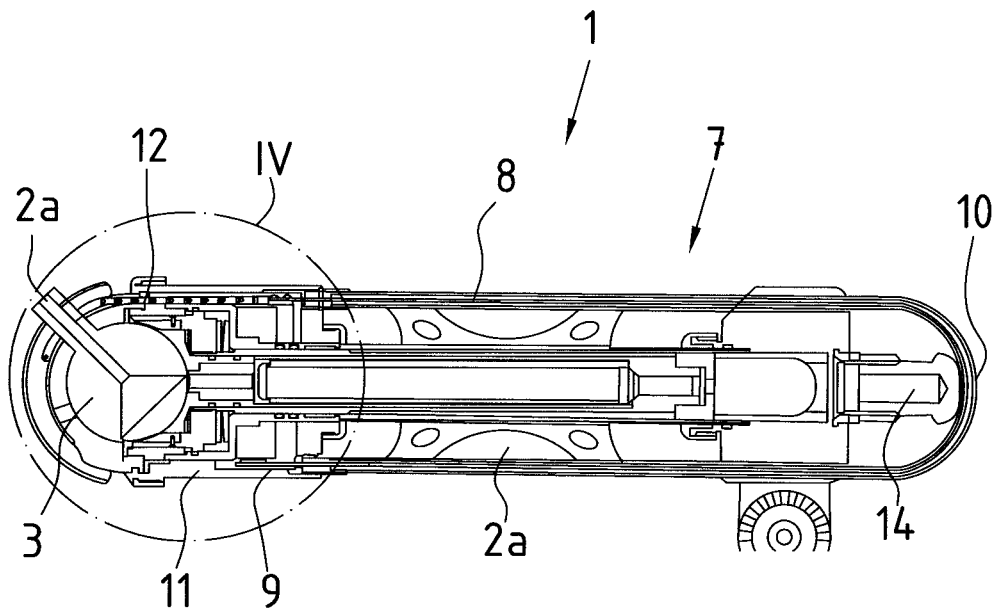
FIG. 3 shows a cut-out side view of a partial area of an inventive holding device.
Figure 4:
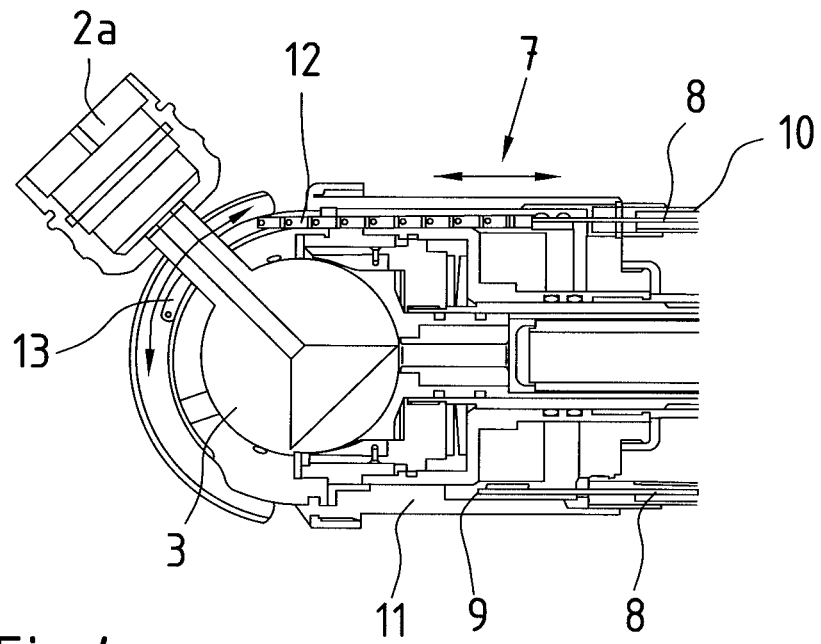
FIG. 4 shows an enlarged view of detail IV according to FIG. 3.

The structure of the inventive weight-relieving system 7 can be seen from FIGS. 2 through 4.

The schematic sketch in FIG. 2 shows the structure and mode of operation of the weight-relieving system 7 described in greater detail hereinafter. The sketch indicates a joint 3 and bracket part 2a that is connected to pivot with the joint 3. Said joint 3 can, for example, be the joint 3 by which the holding device 1 is mounted so that it can pivot, on an operating table 5, on the ceiling, on a wall or on the floor.

The illustrated weight-relieving system 7 consists of a resetting element 8 that is configured as a cable winch 8 and is mounted with one end on the bracket part 2a that can pivot by means of the joint 3 and the other end on a stationary abutment 9.

The cable winch 8 itself consists of a wire of a shape-memory alloy that includes a plateau stress, such as NiTiNoI. Such alloys are characterized in that, on the one hand, they are expandable within a length-modifying area specific to the particular material without additional force exertion (tensile stress) or at least without relevant additional force exertion and, on the other hand, they independently resume their original shape and length after removal of the tensile stress.

With the intermetallic alloy NiTiNoI, the stress plateau is in the range of an expansion of 1% to 8%.

The dimensions of the cable winch 8 that constitutes the weight-relieving system 7 and of the mounting point of the cable winch 8 on the pivotable bracket part 2a are such that the cable winch 8, when the bracket 2 is in the non-deflected resting position, is pre-tensed until it reaches the stress plateau by means of the actual weight of the bracket 2 and of the medical instrument mounted thereon, so that further expansion of the cable winch can result, up to the end of the stress plateau, without additional force exertion.

For FIG. 2 this means that on deflecting the bracket part 2a farther to the left an additional tractive force is exerted on the cable winch 8 but that this tractive force is converted into force-free length modification within the stress plateau, so that the operator displacing the holding device 1 can pivot the bracket 2 virtually free of weight. As soon as the bracket 2 is pivoted back into the starting position, the wire of the cable winch 8 contracts back to its original length because of the shape-memory property of the alloy being used.

This reversibly repeatable process makes possible, along with compact structure and low actual weight, the production of a weight-relieving system 7 that can easily be disassembled and reassembled, for example for cleaning purposes.

FIGS. 3 and 4 show a concrete technical configuration of the weight-relieving system 7 described previously with reference to the schematic sketch in FIG. 2.

FIG. 3 shows a section through the bracket part 2a of a holding device 1 for medical instruments. Positioned on the end of the bracket part 2a on the left side of the drawing is a joint 3 configured as a ball and socket joint, by which an adjoining bracket part 2a can be pivoted with respect to the illustrated bracket part 2a.

In the illustrated embodiment, the cable winch 8 that constitutes the weight-relieving system 7 is positioned in a guide tube 10, which in turn is mounted so that it can slide axially in the housing 11 of the bracket part 2a.

Because the stress plateau in which the cable winch 8 can be expanded free of weight constitutes a percent-wise length modification of the total length of the cable winch 8, the absolute length modification turns out to become greater with a greater length of the wire that constitutes the cable winch 8. For this reason, the cable winch 8 is positioned in the housing 11 of the bracket part 2a in such a way that it encloses almost the entire outer contour of the bracket part 2a in the longitudinal direction of the bracket part 2a.

Forming the abutment 9, the cable winch 8 in the lower part of the drawing is mounted with one end stationary on the housing 11 of the bracket part 2a. With the other end, the cable winch 8, bridging the joint 3, is coupled with the bracket part 2a that can pivot by means of the joint 3, so that the two ends of the cable winch 8 are mounted on two different bracket parts 2a.

Alternatively to the illustrated embodiment, it is also possible of course to configure the abutment 9, not on a bracket part 2a, but instead, for example, on a jig 4, by which the holding device 1 is mounted so that it can pivot on the operating table 5, the ceiling, a wall or the floor.

In the illustrated embodiment the cable winch 8 on the sides of the pivotable bracket part 2a is mounted on the pivotable bracket part 2a not directly, but through a flexible element 12 in the form of a link chain 12, ensuring a uniform and non-jerking transmission of the forces exerted by the pivotable bracket part 2a to the cable winch 8 that forms the weight-relieving system 7.

The coupling of the link chain 12 with the pivotable bracket part 2a occurs according to this embodiment, in particular as illustrated in FIG. 4, by a ring 13, which, on the one hand, is connected movably with the link chain 12 and, on the other hand, can be slid onto the pivotable bracket part 2a.

In order for the cable winch 8 to be able, as a weight-relieving system 7, to balance out the actual weight of the holding device 1 together with the medical instrument mounted thereon, after the installation of the bracket 2 the wire that constitutes the cable winch 8 is pre-tensed by an adjustment mechanism 14 until it reaches the stress plateau.

The adjustment mechanism 14 is positioned in the bracket part 2a equipped with the guide tube 10 in such a way that the guide tube 10 which is mounted so that it can slide axially in the housing 11—and indicated at the right in FIG. 3—is pressed away from the abutment 9 by means of the adjustment mechanism 14. Because the cable winch 8 is mounted with one end stationary on the abutment 9 and the actual weight of the bracket 2 acts on the other end, the sliding of the guide tube 10 with the cable winch 8 positioned therein causes an expansion of the cable winch 8.

The dimensions of the cable winch 8 that constitutes the weight-relieving system 7, as well as the attachment point of the cable winch 8 on the pivotable bracket part 2a are measured in such a way that the cable winch 8, with the bracket 2 in the non-deflected resting position, is pre-tensed until reaching the stress plateau by the actual weight of the bracket 2 as well as of the medical instrument positioned thereon, so that the further expansion of the cable winch 8 as far as the end of the stress plateau can occur without additional force being exerted. The fine-tuning until reaching the stress plateau occurs by means of the adjustment mechanism 14.

For the depiction as in FIGS. 3 and 4, this pre-tensing of the cable winch 8 until reaching the stress plateau of the NiTiNoI wire being used means that on deflecting the pivotable bracket part 2a farther to the left an additional tractive load is exerted on the cable winch 8, but this tractive load is converted into a weight-free length modification of the cable winch 8 inside the stress plateau, so that the operator displacing the holding device 1 can pivot the bracket 2 nearly free of weight. As soon as the bracket 2 is pivoted back into the starting position, the wire of the cable winch 8 contracts back into its original length because of the shape-memory property of the NiTiNoI alloy being used.

A holding device 1 for medical instruments, equipped in such manner with a weight-relieving system 7, is characterized in that the reversibly repeatable process of the weight-free length modification makes it possible to produce a weight-relieving system 7 with a compact structure and a low actual weight, so that the holding device 1 can be easily disassembled and reassembled again and is also completely autoclavable for cleaning purposes.

What is claimed is:

1. A holding device for medical instruments, the holding device comprising:
    a bracket on which at least one medical instrument can be affixed,
    at least one joint to position the bracket, and
    a weight-relieving system to compensate a bracket load, the weight-relieving system being configured as a resetting element coupled with the bracket and made of a material that comprises a plateau stress, the resetting element being pre-tensed by the bracket load until the resetting element reaches the plateau stress, wherein the resetting element is mounted at one end in a non-movable configuration on a first bracket part and at an opposite end on a second bracket part that is displaceable with respect to the first bracket part by the at least one joint;
    wherein the resetting element is disposed in a guide tube that provides guidance of said weight-relieving system, wherein the guide tube is slidable along an axis of a housing of the first bracket part; and
    wherein the resetting element is mounted to the displaceable second bracket part by a flexible element, the flexible element coupled to both the resetting element and the displaceable second bracket part provides a uniform, non-jerking transmission of forces exerted by the displaceable second bracket part to the resetting element.

2. The holding device according to claim 1, wherein the material of the resetting element, which comprises the plateau stress, is selected from a group comprising a CuZnAl, FeNiCoTi and NiTi alloy.

3. The holding device according to claim 2, wherein the material that comprises the plateau stress is a shape-memory alloy.

4. The holding device according to claim 3, wherein the shape-memory alloy that constitutes the resetting element is an NiTiNol alloy.

5. The holding device according to claim 1, wherein the resetting element, bridging the at least one joint, is coupled with the bracket.

6. The holding device according to claim 1, wherein the resetting element is configured as a cable winch.

7. The holding device according to claim 1, wherein the resetting element is configured as a spring element.

8. The holding device according to claim 6, wherein tensing of the cable winch by the slidable guide tube is adjustable.

9. The holding device according to claim 1, wherein the flexible element is configured as a link chain.

10. The holding device according to claim 1, wherein:
the first bracket part has an abutment to which is connected the one end of the resetting element that is mounted in the non-movable configuration; and
the guide tube is configured to be pressed away from the abutment to adjust a tensing of the resetting element.

11. A holding device for medical instruments, the holding device comprising:
a bracket on which at least one medical instrument can be affixed,
at least one joint to position the bracket, and
a weight-relieving system to compensate a bracket load, the weight-relieving system being configured as a resetting element coupled with the bracket and made of a material that comprises a plateau stress, the resetting element being pre-tensed by the bracket load until the resetting element reaches the plateau stress, wherein the resetting element is mounted at one end in a non-movable configuration on a first bracket part and at an opposite end on a second bracket part that is displaceable with respect to the first bracket part by the at least one joint;
wherein the resetting element is disposed in a guide tube that provides guidance of said weight-relieving system, wherein the guide tube is slidable along an axis of a housing of the first bracket part; and
wherein the resetting element within the guide tube is positioned on an outer contour of the first bracket part.

12. The holding device according to claim 11, wherein the material that comprises the plateau stress is a shape-memory alloy.

13. The holding device according to claim 11, wherein the resetting element, bridging the at least one joint, is coupled with the bracket.

14. The holding device according to claim 11, wherein the resetting element is configured as a cable winch.

15. The holding device according to claim 14, wherein tensing of the cable winch by the slidable guide tube is adjustable.

16. The holding device according to claim 11, wherein the resetting element is configured as a spring element.

17. The holding device according to claim 11, wherein the flexible element is configured as a link chain.

18. The holding device according to claim 11, wherein:
the first bracket part has an abutment to which is connected the one end of the resetting element that is mounted in the non-movable configuration; and
the guide tube is configured to be pressed away from the abutment to adjust a tensing of the resetting element.

\* \* \* \* \*